United States Patent [19]

Shibanai et al.

[11] 4,356,115

[45] Oct. 26, 1982

[54] FRAGRANT SYNTHETIC RESIN PRODUCT AND METHOD OF PRODUCING THE SAME

[76] Inventors: Ichiro Shibanai; Kouki Horikoshi, both of Tokyo; Nobuyuki Nakamura, Kunitachi, all of Japan

[21] Appl. No.: 267,969

[22] Filed: Apr. 27, 1981

[51] Int. Cl.³ .............................................. A61K 7/46
[52] U.S. Cl. ........................... 252/522 A; 252/522 R; 428/905; 527/300; 527/313
[58] Field of Search ..................... 252/522 A, 522 R; 428/905; 239/53; 260/9, 17.4 ST; 527/300, 313

[56] References Cited

U.S. PATENT DOCUMENTS

| | | | |
|---|---|---|---|
| 2,808,381 | 10/1957 | Stone ............................ | 260/17.4 ST |
| 4,018,233 | 4/1977 | Miyake ......................... | 260/17.4 ST |
| 4,045,388 | 8/1977 | Matsunaga et al. ......... | 260/17.4 ST |
| 4,169,079 | 9/1979 | Tabashi et al. .............. | 260/17.4 ST |

*Primary Examiner*—John F. Niebling
*Attorney, Agent, or Firm*—Jordan and Hamburg

[57] ABSTRACT

A dry-pulverized cyclodextrin inclusion compound which includes a perfume material is mixed with a thermoplastic synthetic resin to provide a synthetic resin product having a long lasting fragrance.

4 Claims, No Drawings

FRAGRANT SYNTHETIC RESIN PRODUCT AND METHOD OF PRODUCING THE SAME

BACKGROUND OF THE INVENTION

The present invention relates to a synthetic resin product having a fragrance which lasts for a long period of time and a method of producing the same.

The inventors have made various attempts for the purpose of developing a fragrant resin product. However, a perfume material used for imparting the fragrance generally has a high volatility, is easily denatured and is unstable against heat. Accordingly, it has been quite difficult to incorporate a perfume material in the molding step of synthetic resins.

The inventors noted that if a perfume material having the above defects is converted to an inclusion compound with cyclodextrin or a cyclodextrin-containing amylolyzate, it is chemically remarkably stabilized and made resistant to a high temperature of 160°-260° C. and, in addition, dispersibility and compatibility thereof in the step of the incorporation in a synthetic resin are also remarkably improved. After investigations made for the purpose of providing a synthetic resin product having a fragrance which is unchanged and lasts for a long period of time and a method of producing the same by mixing a dry, pulverized inclusion compound comprising a perfume material and cyclodextrin with a thermoplastic synthetic resin material and molding the mixture, the inventors have developed the present invention.

For the production of the above cyclodextrin, processes disclosed in Japanese Patents Nos. 886,583 and 914,137 and Japanese Patent Publication No. 31223/1978 are preferred from an industrial viewpoint with respect to the costs and quantities (scales). In addition, there may also be used cyclodextrin obtained by the reaction of cyclodextrin glycosyl transferase produced by bacteria of Klebsiella and Micrococcus such as *Bacillus macerans, Bacillus circurans* and *Bacillus megaterium* with starch.

DETAILED DESCRIPTION OF THE PREFERRED EMBODIMENTS:

Embodiments of the fragrant synthetic resin products according to the present invention will be shown below:

EXAMPLE 1

Lavender oil was mixed with cyclodextrin. Thus resulting inclusion compound of lavender oil/cyclodextrin was dried and pulverized. The powder was then mixed with a synthetic resin molding material. The mixture was then molded to obtain a synthetic resin product having a fragrance of lavender.

EXAMPLE 2

A synthetic resin product having a mothproofing effect was obtained in the same manner as in Example 1 except that lavender oil was replaced with citronella oil.

The detailed description will now be made on the method of producing fragrant synthetic resin products according to the present invention with reference to the following examples.

EXAMPLE 3

85 Parts by weight of $\alpha$-cyclodextrin were added to 15 parts by weight of geraniol and the whole was stirred at a temperature kept at 50° C. for one hour. Thus obtained inclusion compound of geraniol/cyclodextrin was pulverized to obtain particles smaller than 150 mesh by means of a vacuum dryer or spray dryer at a drying temperature of 60° C. 10 Parts by weight of the powder thus obtained were mixed with 90 parts by weight of polyethylene molding pellets and the mixture was molded into the following various moldings:

(1) Cups, brush cases, brushes and toys having rosy fragrance were produced by injection molding.
(2) Packing films having rosy fragrance were produced by inflation method.

The elegant rosy fragrance of those moldings lasted for longer than a half year without any change in fragrance. Particularly, a pocket tissue paper pack placed in a bag made of above film (2) had a longering scent from the bag and could be used comfortably.

EXAMPLE 4

The following various moldings were obtained from a mixture of 5 parts by weight of the powdery inclusion compound obtained in the same manner as in Example 3 and 95 parts by weight of 6-nylon molding pellets:

(4) Wigs having rosy fragrance were produced from fibers obtained by melt spinning.
(5) A textile cloth having rosy fragrance was produced from fibers obtained by melt spinning and then clothes, umbrellas, wrapping cloths and curtains were made from the cloth.

The elegant rosy fragrance of those moldings lasted for longer than a half year without any change in fragrance.

EXAMPLE 5

A polyethylene film having a mothproofing effect was prepared by the same inflation method as in Example 3-(2) except that geraniol was replaced with dimethyl phthalate. The mothproofing effect lasted for nearly one year.

EXAMPLE 6

10 Parts by weight of the powdery inclusion compound obtained in the same manner as in Example 3 were mixed with 90 parts by weight of polyethylene molding pellets. The mixture was injection-molded to obtain a fragrant adapter to be inserted into a telephone transmitter which had a solid structure comprising a disc base having perforations of a desired shape arranged to form a figure.

The elegant rosy fragrance of the molding lasted for longer than a half year without any change in fragrance.

The preparation and the pulverization of the inclusion compounds in the above examples are desirably carried out at a temperature below 60° C. so as to prevent the denaturation of the perfume material.

The perfume materials used in the present invention are not limited to those used in the above examples but the perfume include all natural and synthetic perfume materials capable of forming inclusion compounds with cyclodextrin. As the cyclodextrin, there may be used $\beta$-cyclodextrin and $\gamma$-cyclodextrin as well as amylolysis products containing $\alpha$-, $\beta$- and $\gamma$-cyclodextrins in addition to or in place of $\alpha$-cyclodextrin used in the foregoing examples. As the synthetic resins, there may be used all sorts of thermoplastic synthetic resins. Among them, those having a relatively low melting point and a high permeability are preferred for preventing the denaturation of the perfume material and for imparting a sufficient fragrance. Further, the long lasting fragrance can be imparted also to a highly variable synthetic resin by adding calcium carbonate or starch thereto in the molding step so as to impart permeability and foaming properties thereto. When a colored product is to be obtained, it is preferred to use a coloring agent in the form of powdered cyclodextrin inclusion compound thereof having a remarkably improved compatibility with the synthetic resin. The coloring thus obtained is better and more stable than that obtained by using the coloring agent as it is.

A coloring agent unstable to untraviolet rays such as a fluorescent paint can also be used if it is converted to an inclusion compound with cyclodextrin to color the synthetic resin in a characteristic color.

As described above, according to the method of producing the synthetic resin product of the present invention, the synthetic resin product having a stable fragrance lasting for a long period of time without changing the fragrance can be provided easily while an expensive perfume material is used in an economically advantageous manner. The effect of the present invention is thus quite remarkable.

What is claimed is:

1. A fragrant synthetic resin product comprising a cyclodextrin and a perfume material which are physically mixed to form a dry-pulverized cyclodextrin inclusion compound containing said perfume material, and a thermoplastic synthetic resin material which is physically mixed with said dry-pulverized cyclodextrin inclusion compound to form a molding mixture, said molding mixture being molded to form said product.

2. A method of producing a fragrant synthetic resin product comprising physically mixing cyclodextrin with a perfume material to form a dry-pulverized cyclodextrin inclusion compound containing said perfume material, dry-pulverizing said compound to form a powder, physically mixing said powder with a thermoplastic resin material to form a molding mixture, and molding said molding mixture to form said product.

3. A fragrant synthetic resin product comprising cyclodextrin-containing amylolyzate and a perfume material which are physically mixed to form a dry-pulverized cyclodextrin-containing amylolyzate inclusion compound containing said perfume material, and a thermoplastic synthetic resin material which is physically mixed with said dry-pulverized cyclodextrin-containing amylolyzte inclusion compound to form a molding mixture, said molding mixture being molded to form said product.

4. A method of producing a fragrant synthetic resin product comprising physically mixing cyclodextrin-containing amylolyzate with a perfume material to form a dry-pulverized cyclodextrin-containing amylolyzate inclusion compound containing said perfume material, dry-pulverizing said compound to form a powder, physically mixing said powder with a thermoplastic synthetic resin material to form a molding mixture, and molding said molding mixture to form said product.

* * * * *